United States Patent [19]
Rogers et al.

[11] Patent Number: 5,734,470
[45] Date of Patent: Mar. 31, 1998

[54] DEVICE AND METHOD FOR TIME-RESOLVED OPTICAL MEASUREMENTS

[75] Inventors: John A. Rogers, Castle Rock, Colo.; Keith A. Nelson, Newton, Mass.

[73] Assignee: Massachusetts Institute of Technology, Cambridge, Mass.

[21] Appl. No.: 844,850

[22] Filed: Apr. 22, 1997

Related U.S. Application Data

[63] Continuation of Ser. No. 377,310, Jan. 24, 1995, abandoned.

[51] Int. Cl.$^6$ .................................. G01B 9/02; G01N 21/00
[52] U.S. Cl. ............................................. 356/354; 356/432
[58] Field of Search .................................... 356/354, 355, 356/432, 237

[56] References Cited

U.S. PATENT DOCUMENTS

| | | |
|---|---|---|
| 4,655,547 | 4/1987 | Heritage et al. |
| 5,062,693 | 11/1991 | Beratan et al. |
| 5,132,824 | 7/1992 | Patel et al. |
| 5,220,403 | 6/1993 | Batchelder et al. ............ 356/345 |
| 5,263,039 | 11/1993 | Skupsky et al. |
| 5,285,438 | 2/1994 | Marchand et al. |
| 5,344,236 | 9/1994 | Fishman ........................ 356/237 |
| 5,479,256 | 12/1995 | Tamai et al. .................. 356/346 |

*Primary Examiner*—Frank G. Font
*Assistant Examiner*—Amanda Merlino
*Attorney, Agent, or Firm*—Fish & Richardson P.C.

[57] ABSTRACT

An optical modulating system which allows modulation of a single light beam with a spatially filtering mask to form a spatially periodic, time-dependent excitation field. Once generated, the field can be used to induce a transient grating in a sample. The optical modulating system is additionally configured to automatically orient a probe beam at the Bragg angle, thereby allowing the intensity of the probe beam diffracted off the induced grating to be maximized. Measurement of the diffracted probe beam allows, for example, determination of mechanical, thermal, electrical, and optical properties of the sample.

32 Claims, 7 Drawing Sheets

Distance Along Z

FIG. 4B

Distance Along Z

Distance Along Z

DEVICE AND METHOD FOR TIME-RESOLVED OPTICAL MEASUREMENTS

This is a continuation of application Ser. No. 08/377,310, filed Jan. 24, 1995, now abandoned.

This invention was made with government support under Grant Number 9317198-DMR awarded by the National Science Foundation. The government has certain rights in the invention.

FIELD OF THE INVENTION

This invention relates to the measurement of material properties using time-dependent, spatially varying optical fields.

BACKGROUND

Measurement techniques involving optical excitation and detection of material motions are extremely important from both purely scientific and applications-oriented points of view. In particular, techniques such as transient grating spectroscopy or impulsive stimulated scattering use laser light to both excite materials (e.g., polymer films) and to measure the resulting response. In these techniques two excitation laser pulses are crossed in space and time in the sample. Overlap of the excitation pulses results in optical interference to produce an excitation field which has alternating "light" and "dark" regions, with the overall intensity of the field varying in a sinusoidal manner. The angle between the overlapping pulses determines the spatial frequency, i.e., the wavevector, of the alternating regions.

The excitation field can induce a transient grating in the sample through several different mechanisms. For example, optical absorption of the excitation field can create electronic excited states which can decay through the emission of heat or light. For example, in Impulsive Stimulated Thermal Scattering ("ISTS") the optical energy of the light regions of the field is absorbed by the sample, resulting in the deposition of heat which is followed by thermal expansion of the irradiated regions. This results in the launching of coherent, counter-propagating ultrasonic phonons having a wavevector with a spatial frequency and orientation matching the geometry of the excitation field. The sample can also be excited via a non-absorptive process. In Impulsive Stimulated Brillion Scattering ("ISBS") or Impulsive Stimulated Raman Scattering ("ISRS"), for example, the sample is excited using a spatially varying optical intensity pattern, but the photons have a wavelength that is not absorbed by the film. In these techniques, optical energy is coupled directly into the film's acoustic field to excite acoustic processes. The excitation process takes advantage of the inherent spectral line width of the excitation pulses; higher-frequency photons from each excitation pulse are annihilated to create lower-frequency photons in the opposite excitation pulse. Counter-propagating acoustic phonons of the difference frequency and wavevector are then generated in the medium.

In ISTS, ISRS, ISBS, and other transient grating techniques, phonon propagation or electronic events may continue after the excitation pulses leave the sample, causing a time-dependent, spatially periodic variation in the material properties in the excited region. Because the relevant optical properties of the material are functions of the magnitude of this response, the time dependence of the excited region can be detected with an optical probe beam. The excited region of the sample functions as a transient diffraction grating, resulting in diffraction and modulation of the incident probe beam to produce a signal beam which can be detected and analyzed. In order to determine a particular property of the sample, such as the elastic moduli, it may be necessary to measure the sample's dispersion (i.e., the wavevector-dependent response).

In order to form the spatially varying optical excitation field using the conventional transient grating methodology, the excitation beam is split into two beams, which are then recombined in the sample using optical components such as mirrors, beam-splitters, lenses and mechanical delay stages. These components may also be used to adjust the angle between the excitation beams. Additional optical components are used to accurately adjust the angle, spatial overlap, and timing of the probe beam with respect to the excitation beams. However, even after careful adjustment, the signal diffracted by the induced transient grating-is often weak, making both alignment and detection difficult.

SUMMARY

In one aspect, the invention provides a method and apparatus for determining a property of a sample using the steps of: (a) providing a beam of radiation, and then, passing the beam through a pattern on a diffracting mask to form at least two excitation sub-beams; (b) overlapping at least two excitation sub-beams on a region of the sample with an imaging system to generate a spatially varying optical field which excites a transient grating in the region of the sample; (c) irradiating the transient grating with a probe beam oriented so that at least a portion of the probe beam is diffracted by the transient grating; (d) detecting the diffracted portion of the probe beam with an optical detector to generate a light-induced signal; and (e) analyzing the light-induced signal from the optical detector to determine the property of the sample.

By "sub-beam", as used herein, is meant an optical field resulting from diffraction of either an excitation or probe beam. The excitation and probe beams may have the same or different wavelengths; both beams may be partially absorbed by the sample.

In preferred embodiments, the diffracting pattern includes alternating light-modulating regions having at least one spatial frequency, and the excitation beam is separated into at least a zeroth, +1, and −1 excitation sub-beam following diffracting off of the light-modulating regions of the diffracting pattern. In this case, the overlapping step may further include the step of passing at least the +1 and −1 excitation sub-beams through the imaging system (e.g., a lens or series of lenses) prior to overlapping these sub-beams on the sample. The imaging system then images at least one of the spatial frequencies of the light-modulating regions of the diffracting pattern onto the sample to form the spatially varying optical field. Preferably, at least one of the spatial frequencies of the light-modulating region and the spatial varying optical field are equivalent.

In still other preferred embodiments, the probe and excitation beams are made collinear prior to step (a). In this case, step (a) further comprises the step of separating the probe beam into at least two probe sub-beams by passing the probe beam through the diffracting pattern on the first mask. Here, the probe sub-beams preferably pass through the imaging system prior to irradiating the grating induced in the region of the sample.

In other preferred embodiments, the excitation beam is focussed (e.g., cylindrically focussed) onto the diffracting pattern prior to step (a). In addition, the imaging system is preferably a 1:1 imaging system. In this embodiment, the probe beam irradiates the transient grating at the Bragg angle.

In still other preferred embodiments, between steps (b) and (c), the excitation sub-beams are spatially filtered with a second mask. Preferably, the first and second masks are contained in a single unit, and the spatial filtering transmits the +1 and −1 excitation and probe sub-beams.

In other embodiments, the analyzing step further includes determining the dispersion of the sample. The dispersion may be used to determine the mechanical (e.g., adhesion, elastic moduli, stiffness, residual stress, and density), thermal, optical, or electronic properties of the sample. In this embodiment, the dispersion may be determined following the step of inducing multiple transient gratings in the sample with a single spatial varying optical field having multiple spatial frequencies. Alternatively, the dispersion is determined following the steps of sequentially inducing multiple transient gratings in the sample with multiple spatial varying optical fields, each of which has a single spatial frequency.

In another aspect, the invention provides a method of diffracting a probe beam off a sample. The method includes: (a) providing a beam of radiation, and then passing the beam through a pattern on a diffracting mask to form at least two excitation sub-beams; (b) overlapping at least two excitation sub-beams on a region of the sample with an imaging system to generate a spatially varying optical field which excites a transient grating in the region of the sample; and (c) irradiating the transient grating with a probe beam oriented so that at least a portion of the probe beam is diffracted by the transient grating.

In another aspect, the invention provides an apparatus for diffracting a portion of a probe beam off a sample. The apparatus includes means for generating a probe optical beam and an excitation optical beam orientated along an optical axis, and a first diffracting mask including an optical diffracting pattern. The diffracting pattern is positioned along the optical axis and is configured so that, when irradiated with the excitation beam, the pattern diffracts the excitation beam to generate at least two excitation sub-beams. The apparatus also include an imaging system containing at least one lens positioned along the optical axis. The imaging system is configured to focus the excitation sub-beams onto a region of the sample to generate a spatially varying optical field which excites a transient grating which allows partial diffraction of the probe beam.

In preferred embodiments, the diffracting pattern includes a series of opaque regions spaced by a distance which allows diffraction of visible or infrared radiation. Alternatively, the diffracting pattern may include a series of regions etched to a depth and spaced by a distance which allows diffraction of visible or infrared radiation. Preferably, the diffracting mask includes a plurality of diffracting patterns.

In another preferred embodiment, the apparatus further includes a second, spatially filtering mask which includes a pair of openings. The openings are positioned along the optical axis so that the spatially filtering mask allows spatial filtering of the diffracted excitation sub-beams. Preferably, the spatial filtering mask includes a plurality of pairs of openings, and the diffracting and spatial filtering masks are contained in a single unit.

Embodiments may include one of the following advantages. For example, a simple, linearly configured optical system is provided which modulates a single beam with a filtering mask to form a spatially periodic, time-dependent excitation field which can then be used to induce a transient grating in a sample. The system can be additionally configured to orient a probe beam at the Bragg (or phase-matching) angle using a simple optical arrangement. This allows the diffraction efficiency of the induced grating, and the intensity of the diffracted probe beam, to be maximized.

Optical alignment of the system is both simple and quick. The user need only make the probe and excitation beam collinear prior to interaction with the masks. The masks and imaging optics are used to define the excitation pattern (i.e., wavevector) at the sample, set the timing such that the excitation pulses arrive at the sample at the same time, set the probe angle of incidence at the Bragg angle, and provide a beam to allow for facile signal location and amplification. During operation, the wavevector of the excited phonons can be adjusted simply by translating the masks. These masks are the only moving parts in the system, allowing the measurement technique to be easily automated while reducing the number of optics required in the optical modulating system.

When a thick grating is formed in the sample, automatic setting of the Bragg angle allows the diffraction efficiency of the grating to be maximized. This is particularly important, as diffraction efficiency for these gratings falls off rapidly at angles even within a fraction of a degree of the Bragg angle, regardless of the amplitude of the material response. Once irradiated, the optical modulating system generates multiple probe beams at the sample. One probe beam can serve to probe the transient grating, while another probe beam may serve as a "finder" beam to determine the position of the signal beam. This makes the practical matter of aligning weak signals into a detector trivial since the finder beam has a large optical intensity, and is thus easy to locate. This same finder beam may also be used for heterodyne amplification of weak signal beams.

Moreover, with this invention the excitation fields are not limited to simple sinusoidal patterns. For example, in some cases it may be desirable to induce material motions with more complex geometries or to simultaneously excite material motions at multiple wavevectors using complex mask patterns.

DETAILED DESCRIPTION

Figure 1:
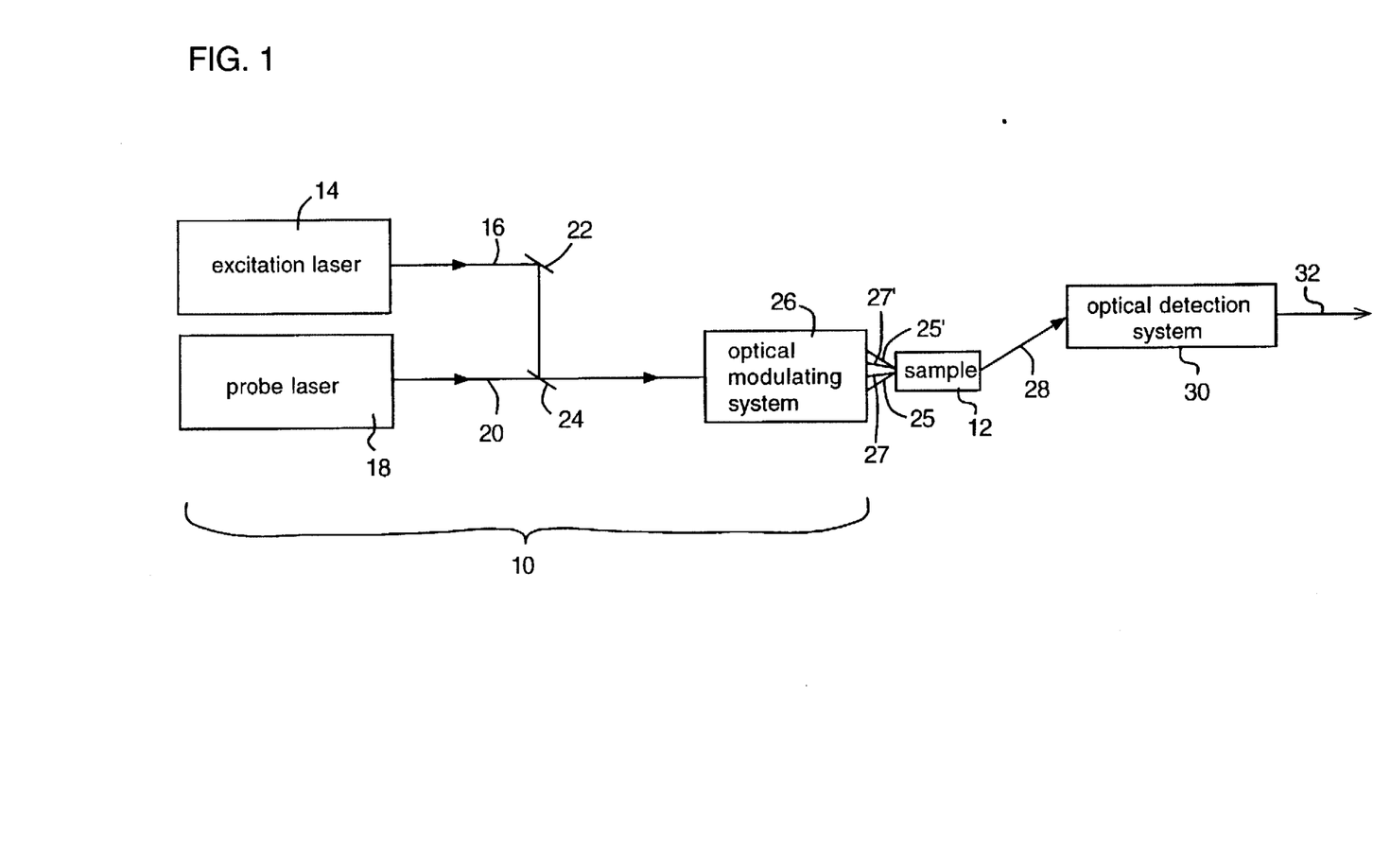
FIG. 1 is a schematic drawing of the optical elements of a sample-measuring device according to the invention.

Referring to FIG. 1, an optical measurement system 10 used to excite a sample 12 and probe the resulting motions includes excitation 14 and probe 18 lasers which produce, respectively, excitation 16 and probe 20 optical beams. The excitation beam is composed of a sequence of pulses, while the probe beam may contain sequences of pulses, or alternatively, optical waveforms having relatively long temporal durations. Prior to irradiating the sample, the excitation beam 16 is reflected by a pair of optics 22, 24 which are highly reflective at the excitation beam wavelength and are oriented to direct the beam into an optical modulating system 26. The second high-reflecting optic 24 preferably reflects the excitation beam efficiently, and is partially transparent to the probe beam. For example, this optic may be a beamsplitter, dichroic mirror, or a thin film polarizer. The optic 24 allows the probe beam 20 to be oriented collinearly with the excitation beam 16 prior to entering the optical modulating system 26.

The optical modulating system 26 modulates the single excitation beam 16 to produce a pair of spatially modulated excitation sub-beams 25, 25' which are recombined within or on the surface of the sample. The optical modulating system is configured so that the timing and spatial positions of the pulses in the excitation sub-beams 25, 25' are overlapped, resulting in optical interference between the two sub-beams to produce a spatially varying optical field which is then used to excite the sample 12. The single probe beam 20 is also spatially modulated by the optical modulating system 26, resulting in the generation of a pair of probe sub-beams 27, 27' which, when the probe wavelength is different than the excitation wavelength, spatially separate from the excitation sub-beams 25, 25'. During the measurement process, both probe sub-beams 27, 27' are diffracted from the transient grating excited in the sample, resulting in the generation of a pair of signal beams. A single signal beam 28 is measured by an optical detection system 30, which may include, for example, a photodetector electrically connected to a transient recording device. Measurement of the diffracted signal results in the generation of a status signal 32 which may be further processed by a computer and used to evaluate the material properties of the sample 12.

The elements of the optical modulating system 26 generate the spatially varying optical excitation field from a single excitation beam, and allow the Bragg angle of incidence of the probe beam to be automatically set. This permits data to be collected at a variety of excitation wavevectors with minimal alignment, thereby allowing the dispersive characteristics of the sample to be easily measured. Measurement of the dispersion allows, for example, material properties such as modulus of elasticity, thermal diffusion, adhesion, electronic transport, and stress to be determined in both bulk and thin film samples. In addition, the optical modulating system 26 has a simple, compact design with a minimal number of optical elements, and only one movable element. This allows the sample-measurement process to be easily automated and performed in a rapid fashion.

Figure 2:
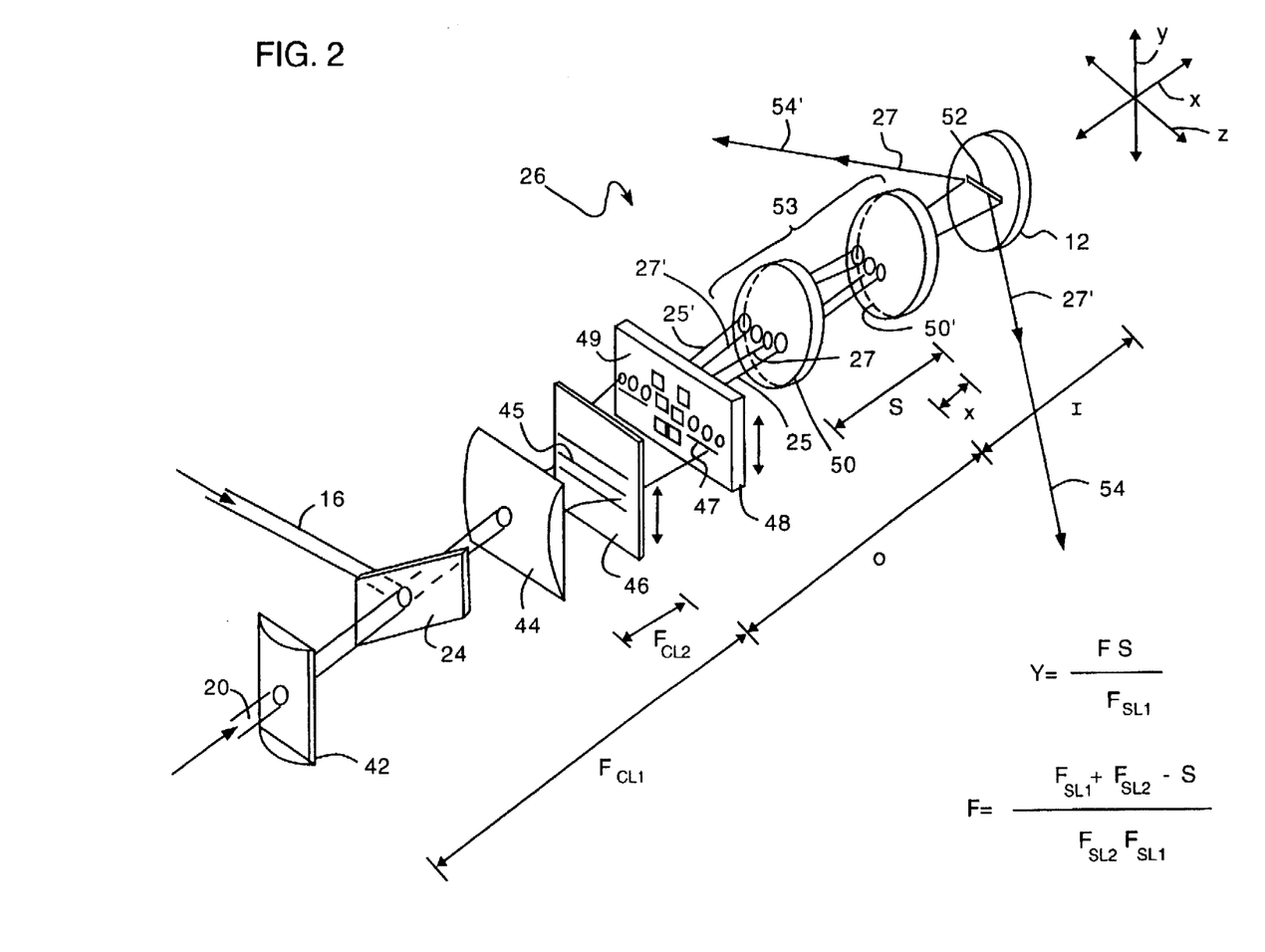
FIG. 2 is a perspective view of the optical modulating system of the sample-measuring device.
Figure 3:
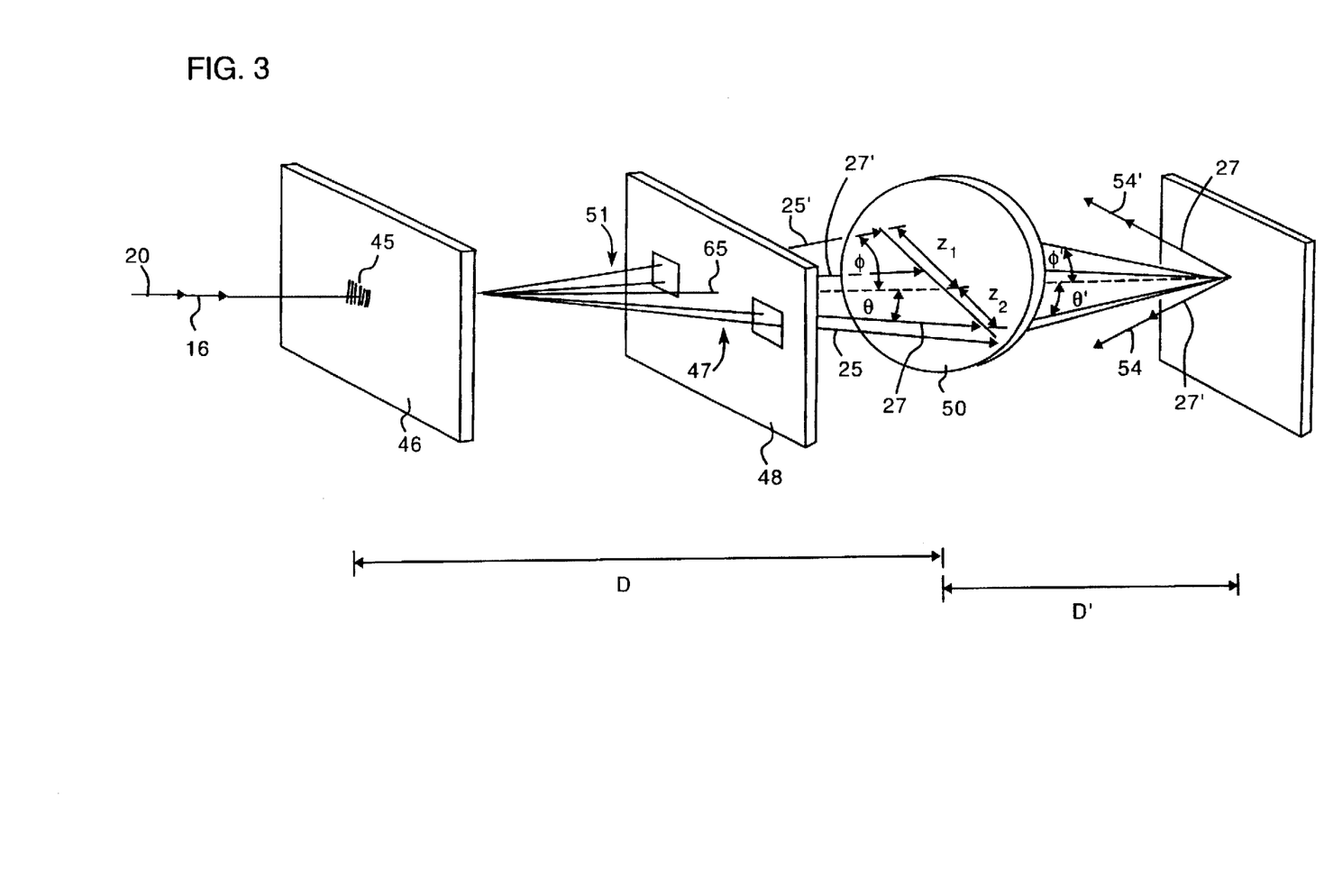
FIG. 3 is an expanded view of the masks and imaging optics of the optical modulating system.

Referring now to FIGS. 2 and 3, in a preferred embodiment, the elements of the optical modulating system 26 are preferably disposed in a linear arrangement along an axis (indicated in the figure by the x axis) to allow spatial modulation of the collinear excitation 16 and probe 20 beams. Prior to passing through the optic 24, the probe beam 20 is transmitted through a first cylindrical lens 42 (having a focal length indicated by "$F_{c11}$") which focuses the beam so that it is elongated along the z axis. Once overlapped, the excitation 16 and probe 20 beams are focussed with a second cylindrical lens 44 (having a focal length indicated by "$F_{c12}$") onto a patterned region 45 of a first mask 46 which spatially filters both beams. The mask 46 is positioned at the focal point ($F_{c12}$) of the second cylindrical lens 44 so that the excitation beam is focussed to an elongated, elliptical spot which extends along the pattern 45, while the probe beam, previously focussed with the first cylindrical lens 42, is focussed to a small circular spot in the center of the elongated excitation spot.

The patterned region 45 on the mask 46 may include, for example, an alternating periodic pattern of transmissive and opaque regions which filter the intensity of the cylindrically focussed excitation beam. Alternatively, the pattern may include periodic regions of transparent glass etched to varying depths (e.g., $\lambda/4$) which filter the phase of the incident excitation field. In both cases, interaction of the excitation 16 and probe 20 beams with the patterned region 45 causes diffraction of these beams to form a series of sub-beams corresponding to different diffractive orders.

After being dispersed and separated following diffraction from the first mask 46, the diverging excitation and probe sub-beams are spatially filtered by a second mask 48 which is displaced along the x axis from the first mask by a distance which allows clear spatial separation of the excitation and probe diffractive orders. This is the case when the wavelengths of the excitation and probe beams are different; when the wavelengths are the same, the excitation and probe sub-beams are not separated. The second mask 48 includes multiple pairs of openings 49, 49' which allow transmission of the selected diffractive orders from both the pump and probe beams. Preferably, the second mask is configured so that each pair of openings corresponds to a separate patterned region on the first mask. The pairs of openings are brought into the beam path by translating the second mask vertically.

Each diffractive order represents a different Fourier component of the spatially varying pattern region 45 of the first mask 46. For example, the +1 and −1 orders of the excitation and probe fields are first order Fourier components, while higher (e.g., +/−2, +/−3) and lower (e.g., the zeroth order) diffractive orders represent, respectively, high-frequency and DC Fourier components. Spatial filtering by the second mask 28 thus allows selected Fourier components of the diffracted field to pass; these components are then recombined on the sample to form the desired excitation pattern.

The excitation 25, 25' and probe 27, 27' sub-beams are transmitted through the mask 48. The diffracted sub-beams diverge at angles of Θ (probe sub-beams) and φ (excitation sub-beams), with each sub-beam representing either the positive 47 (e.g., +1, +2) or negative 51 (e.g., −1, −2) orders of diffraction. The diffractive process depends on the spatial separation d (i.e., the "wavelength") of the light-modulating regions of the patterned region, and on the wavelengths of the incident excitation and probe fields:

$$2d \sin(\Theta) = n \lambda_{probe}$$

$$2d \sin(\phi) = n \lambda_{excitation} \quad (1)$$

where n is the diffracted order. Thus, the divergence of the sub-beams is determined only by the excitation and probe wavelengths and the geometry of the patterned region.

Recombination of the transmitted diffracted orders of the excitation and probe beams is accomplished using an imaging system 53. This allows: 1) spatial recombination of selected excitation sub-beams, resulting in the generation of a spatially varying optical field in or on the surface of the sample; and 2) the probe sub-beams to be automatically oriented so that they arrive at the sample at the Bragg (i.e.

phase-matching) angle. The imaging optics may consist of a single lens (FIG. 3) or two separate lenses 50, 50' having focal lengths of, respectively, $F_{s11}$ and $F_{s12}$ (FIG. 2).

In the case where two separate lenses are used, the separation between the lenses, indicated by S in the figure, allows the imaging system to be used as a telescope to magnify or demagnify the field imaged onto the sample. This allows the spatial scale or size of the interference pattern at the sample to be adjusted by changing the separation between the two imaging lenses. For example, if the interference pattern is demagnified on the sample, the separation between light and dark regions will be decreased, resulting in an increase in the excitation wavevector. Conversely, if the pattern is magnified, the separation between light and dark regions is increased, and the spatial frequency of the excitation wavevector is decreased.

The actual imaging process occurs at a plane defined as the image plane, which is determined by the focal length of a single lens or the equivalent focal length of the multiple-lens (e.g., a two-lens) imaging system. In the two-lens system, the effective focal length F of the imaging system is a function of $F_{s11}$, $F_{s12}$, and S:

$$F = \frac{F_{s11} + F_{s12} - S}{F_{s11} F_{s12}} \quad (2)$$

The effective "position" X of the imaging system along the x axis is displaced from the second lens 50' by a distance related to F, S, and the focal length $F_{s11}$ of the first lens 50:

$$X = \frac{FS}{F_{s11}} \quad (3)$$

The patterned region on the mask, which represents the object to be imaged, is displaced from X by a distance O. The displacement I of the sample from X represents the displacement of the image plane, and is related to F and O by the equation:

$$\frac{1}{F} = \frac{1}{O} + \frac{1}{I} \quad (4)$$

which can be rewritten as $$I = \frac{OF}{(O-F)} \quad (5)$$

Thus, during imaging, the degree of magnification or demagnification M of the object, defined as M=I/O, can be adjusted by choosing a lens combination which gives the desired value of F, and by placing the sample at the appropriate distance I from X.

In addition to imaging particular Fourier components of the patterned region onto the sample, the imaging optics can be configured to focus the transmitted probe beams onto the induced grating at the Bragg angle. Referring now to FIG. 3, in order for the probe beam 16 to satisfy the Bragg phase-matching criteria, excitation 20 and probe 16 beams having wavelengths $\lambda_{ex}$ and $\lambda_{pr}$ are spatially overlapped along an optical axis of the modulating system prior to irradiating the patterned region 45 on the first mask 46. (In this embodiment, a single imaging lens is used, although it is understood that a multiple-lens imaging system, as shown in FIG. 2, may also be used.) Diffraction generates at least a zeroth 65, +1 47, and −1 51 diffracted orders, with each order containing the excitation 25, 25' and probe 27, 27' sub-beams. The excitation and probe beams are separated, respectively, by angles φ and Θ from the optical axis of the sub-system. The second mask 48 is used to spatially filter the zeroth order 65 and transmit the +1 47 and −1 51 orders onto an imaging lens 50 which is spaced a distance D from the first mask 46. The diffracted excitation and probe beams irradiate the lens, respectively, at distances $z_1$ and $z_2$ from the optical axis. The beams are imaged onto the sample 12 which is spaced a distance D from the lens 50. In this configuration, the distances D and D' are related by the equation $$\frac{1}{D'} = \frac{1}{f} - \frac{1}{D} \quad (6)$$

which can be rewritten as $$D' = \frac{Df}{(D-f)} \quad (7)$$

Following focussing by the lens 50, the diffracted orders 47, 51 containing the probe and excitation sub-beams converge on the sample with angles Θ' and φ', which can be related to $z_1$, $z_2$, D, and D':

$$\tan\phi' = \frac{z_1}{D'} = \frac{D\tan\phi}{D'} \quad (8)$$

$$\tan\Theta' = \frac{z_2}{D'} = \frac{D\tan\Theta}{D'} \quad (9)$$

In can be shown, then, that $$\frac{\sin\Theta'}{\sin\phi'} = \frac{\lambda_e}{\lambda_p} \sqrt{\frac{M^2\left[1-\left(\frac{\lambda_e}{2d}\right)^2\right] + \left(\frac{\lambda_e}{2d}\right)^2}{M^2\left[1-\left(\frac{\lambda_p}{2d}\right)^2\right] + \left(\frac{\lambda_p}{2d}\right)^2}} \quad (10)$$

To satisfy the phase-matching criteria, it is required that $$\frac{\sin\Theta'}{\sin\phi'} = \frac{\lambda_e}{\lambda_p} \quad (11)$$

Two conditions must be met, therefore, for the Bragg phase-matching angle to be set independently of the mask pattern.

These conditions are: M=1 (i.e., a 1:1 imaging system), or the case when $$M > \frac{\left(\frac{\lambda_e}{2d}\right)}{\sqrt{1+\left(\frac{\lambda_e}{2d}\right)^2}} \quad (12)$$

and $$M > \frac{\left(\frac{\lambda_p}{2d}\right)}{\sqrt{1+\left(\frac{\lambda_p}{2d}\right)^2}} \quad (13)$$

hold for the imaging system. In addition, in the case where the excitation and probe wavelengths are equivalent, the Bragg angle for the system is automatically set using the optical modulating system.

Thus, by making the excitation and probe beams collinear prior to entering the optical modulating system, the probe beam is diffracted by the first mask to produce a pair of probe sub-beams which, when conditions (1) or (2) are satisfied, are automatically oriented at the Bragg angle.

Following interaction with the transient grating, the sub-beams incident on the sample are diffracted to generate a pair of signal beams 54, 54' which are spatially overlapped with the residual portions (i.e., the non-diffracted components) of the opposing probe sub-beams. The presence of both diffracted (i.e., signal) and reflected (i.e., residual probe) beams is advantageous for two principal reasons. First, the residual beam may be used as a reference or "finder" beam which allows the spatial location of the signal (which is often weak and hard to see by eye) to be determined, thereby simplifying alignment of the diffracted beam into the detection apparatus. Second, the presence of both signal and reference beams allows for heterodyne amplification of the signal beam, i.e., the high-intensity residual beam may be used to optically interfere and "beat" against the weak diffracted signal beam, resulting in amplification of the signal. Although FIGS. 2 and 3 show a sample which reflects the incident probe beams, transmissive samples may be monitored; the relative geometries for the excitation, probe, and signal beams are similar for such samples.

Figure 4A:
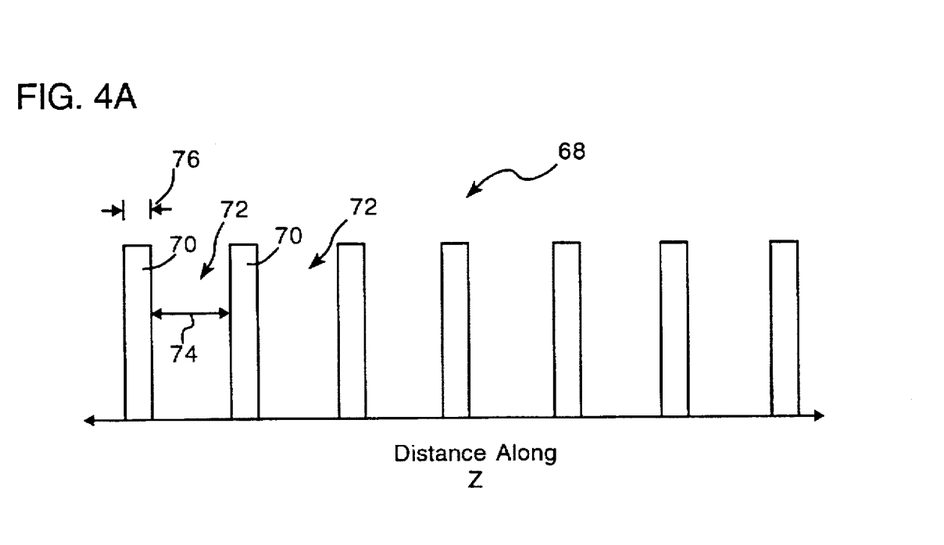
FIGS. 4A and 4B are, respectively, a graph showing the spatial dependence of the modulating regions of the mask, and the spatial dependence of the excitation field generated using the diffracting mask of the optical modulating system.
Figure 4B:
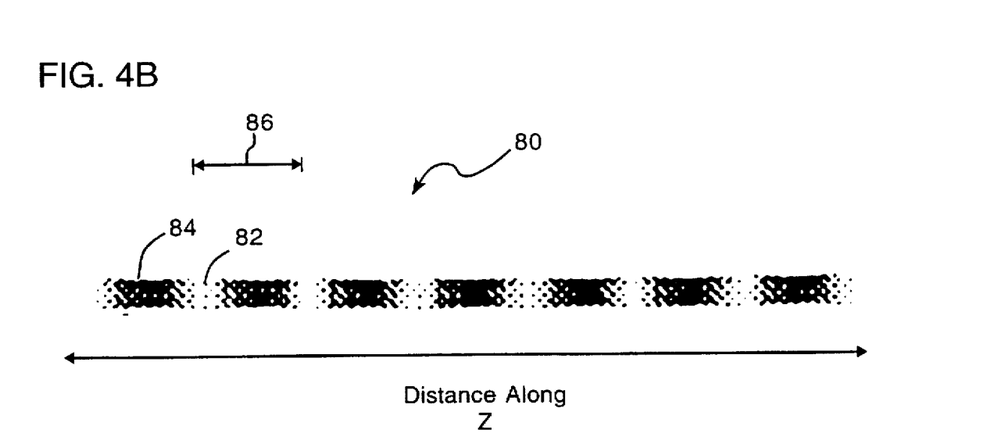

Referring now to FIGS. 4A and 4B, the patterned region 68 of the first mask of the optical modulating system interacts with the incident excitation field to produce multiple orders of excitation sub-beams, which can then be recombined to generate a spatially varying optical field at the sample. In a preferred embodiment, the patterned region 68 consists of alternating, equally spaced opaque regions 70, each having a width 76, which are separated from each other by neighboring transparent regions 72. The modulating regions 70 of the mask may consist, for example, of a series of opaque lines formed by deposition of an absorbing material, such as a thin metal film, on a glass substrate which is transparent to the excitation and probe laser wavelengths. Masks having this "square-wave" transmission profile include, in theory, an infinite number of spatial frequency components, and will thus produce an infinite number of diffracted orders, with the intensity of each order falling off as $$I \sim \left[ \left[ \frac{\sin\left(\frac{N\pi dp}{\lambda}\right)}{\sin\left(\frac{\pi dp}{\lambda}\right)} \right]^2 \frac{\sin\left(\frac{\pi sp}{\lambda}\right)}{\frac{\pi sp}{\lambda}} \right]^2 \quad (14)$$

where $\lambda$ is the wavelength of light, $p=\sin\Theta$, where $\Theta$ is the diffracted angle, n is the diffracted order, and d is the width of the opaque regions, and s is the distance separating these regions. Multiple orders appear because Fourier decomposition of the square-wave pattern of the mask yields an infinite additive series of sine wave harmonics, with the fundamental frequency of the series equivalent to the inverse of the spacing 74.

Alternatively, the modulating regions 70 of the mask may be fabricated to have a different thickness relative to the transparent regions 72 so as to spatially modulate the phase of the excitation field. For example, if the region 70 of the pattern 68 is etched so that its thickness is $\lambda/2$ less than the thickness of the adjacent regions 72, then the portions of the cylindrically focussed excitation spot which propagate through regions 70 will be $\pi$ out of phase relative to the adjacent portions of the excitation field following propagation through the mask. Phase modulation, as opposed to amplitude modulation, may be desirable as a way of modulating the excitation field as the intensity of the field is not attenuated by the mask.

Both the amplitude and phase-modulating masks diffract the excitation field into multiple sub-beams. Once when recombined in or on the sample, the excitation sub-beams result in an optical interference pattern in which the spatial separation 86 of the light 82 regions (or, alternatively, dark regions 84) of the optical intensity pattern 80 is a function of the spacing 74 in the patterned region 68 and, as described above, the focal and geometric properties of the imaging system.

In general, the spacing 74 of the regions 70 on the pattern 68 is within a factor of between 1 and 1000 of the wavelength of the optical field 80 which is imaged in the sample; typically the spacing is between 1 and 100 microns. A single mask may include multiple patterns, with each pattern having a different spacing 74 between light-modulating regions 70 and thus corresponding to an excitation field having a different wavevector. The multiple patterns are preferably placed as close together as possible; for typical beam geometries, individual patterns are preferably separated by distances of between about 300–700 microns. The width 76 of the modulating regions is typically between 0.2 and 1.5 times the separation distance 74.

In the case where it is desirable to excite multiple acoustic modes in the sample, with each mode having a separate well-defined wavevector, a patterned region on the mask may be fabricated to include multiple low-frequency spatial frequency components (i.e., frequencies other than those used to construct the square wave edges). For example, the mask may have multiple square or sine waves, each having a different periodicity. An excitation field having this pattern will excite multiple modes, allowing the dispersive (i.e., wavevector-dependent) properties of the sample to be determined using a single excitation pulse.

The shape of the modulating regions 70 of the pattern 68 need not have a square-wave profile. For example, the pattern may vary sinusoidally along the z dimension. This geometry, as opposed to the square-wave pattern which essentially requires an infinite number of spatial frequencies to construct the sharp edges of the waveform, contains only a single frequency component equal to the spatial frequency of the sine wave. The intensity of the field diffracted by the sine wave pattern is primarily distributed between a DC component (i.e., the zeroth order) and the +1 and −1 diffractive orders. In this embodiment, therefore, a larger fraction of the incident excitation field is concentrated in the first-order excitation sub-beams.

In another embodiment, multiple masks, each having a different spatial frequency, may be stacked sequentially along the z axis and used to generate an optical field containing multiple excitation wavevectors. In addition, other patterns, such as a series of concentric rings, may also be included on the mask and imaged onto the sample.

The patterned regions of amplitude and phase masks are fabricated using deposition techniques well-known in the art, such as chemical vapor deposition, RF and magnetron sputtering techniques, and standard micro-lithographic (i.e., photo-lithographic) techniques. These methods are described, for example, in *Semiconductor Lithography: Principles, Practices, and Materials*, Wayne M. Moreau (1988), and *Wavefront Engineering for Photolithography*, Mark D. Levinson, the contents of which are incorporated herein by reference. Both square and sine wave patterned masks are also available commercially from, for example, Sine Patterns or Applied Image Inc. Phase-modulating masks may be formed, for example, using glass etching techniques known in the art, such as those described in the above-mentioned references.

Figure 5A:
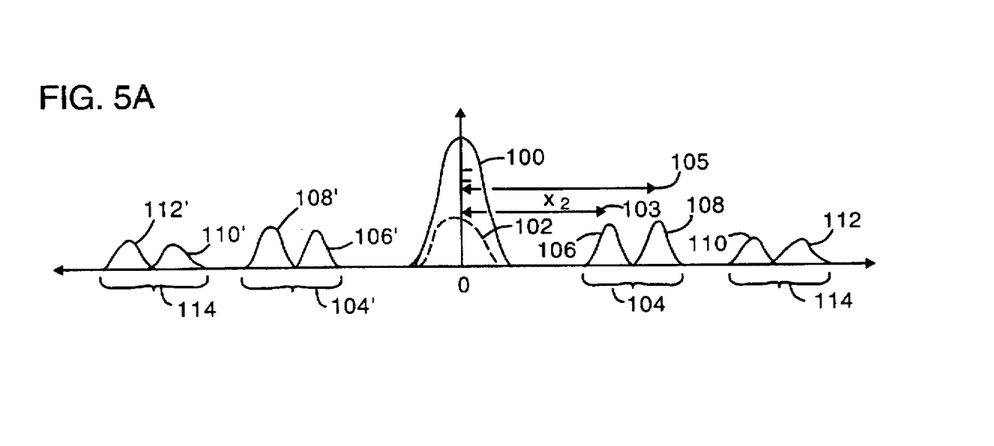
FIGS. 5A, and 5C are, respectively, the spatial dependencies of the excitation and probe fields after being diffracted by the first mask but prior to being filtered by the second mask, and after being diffracted by the first mask and filtered by the second mask.
Figure 5B:
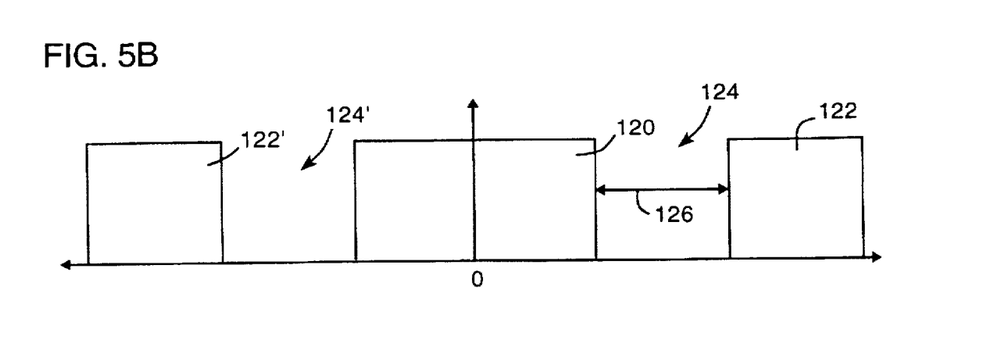
FIG. 5B is the spatial transmission function of the spatial filtering mask.
Figure 5C:
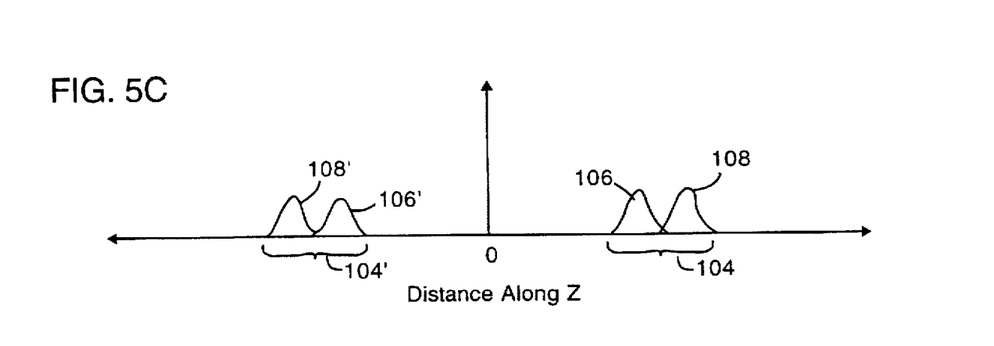

Once the excitation and probe beams are diffracted from the patterned region of the first mask, the second mask is used to spatially filter the diffracted field to allow selection of the diffracted orders which are to be imaged onto the sample. Referring now to FIGS. 5A and 5C, following diffraction by the first mask, the optical intensities of the diverging sub-beams, indicated by the ordinate axes in the figures, vary as a function of the divergence along the z axis. The figures represent the spatial intensity profile of the diffracted excitation and probe sub-beams measured along a plane which is adequately spaced from the first mask, thereby allowing clear separation of the diffracted orders and the sub-beams within each diffracted order. The zeroth diffracted orders 100, 102 of both the excitation and probe sub-beams, representing the spatial DC component of the diffracted field, do not diverge and remain spatially overlapped following interaction with the diffracting mask. The +1 and −1 orders, indicated, respectively, by brackets 104 and 104', contain the +1 and −1 probe 106, 106' and excitation 108, 108' sub-beams. The separations between the DC components 100, 102 and the excitation and probe sub-beams of the +1 and −1 orders, indicated by the arrows 103 and 105, are a function of the configuration of the pattern on the mask, the wavelengths of the excitation and probe fields, and the separation between the plane of the diffracted field and the mask. In the case where the pattern on the diffractive mask is configured to generate multiple diffractive orders (i.e., a square wave diffracting pattern), probe 110, 110' and excitation 112, 112' sub-beams will be present in the +2 and −2 diffractive orders indicated, respectively, by the brackets 114 and 114'. Higher diffracted orders, although possible, are not shown in the figure.

The second mask is chosen to have a transmission function which spatially filters the diffracted pattern, thereby selecting, for example, a single pair of diffractive orders. Referring now to FIGS. 5B and 5C, a mask which allows selection of the +1 and −1 diffractive orders has non-transmissive regions 120, 122, 122' which block the DC and higher-order diffracted components, thereby preventing these sub-beams from propagating onto the sample. Transmissive regions 124, 124' are disposed to allow four beams, i.e., the +1 and −1 orders 104, 104' each containing the excitation 108, 108' and probe 106, 106' sub-beams, to propagate onto the sample. In embodiments, the non-transmissive regions in the second mask may be composed of an absorbing or reflecting substrate, such as a metal or plastic plate, and the transmissive regions may consist of apertures where the substrate has been removed.

The width of the transmissive region in the second mask, indicated by the arrow 126, is chosen to allow passage of both the excitation and probe sub-beams of the selected diffraction order. This width is dependent on the cumulative spatial extension of the diffracted excitation and probe sub-beams, and, as described previously, is determined by the wavelengths of the excitation and probe fields, the spacing of the modulating regions in the diffracting pattern, and the separation between the dispersed fields and the first mask. Typically, the transmissive regions have widths of between 0.5 and 2.0 cm.

During operation, the diffractive patterned regions on the first mask are aligned with respect to the spatial filtering patterns on the second mask so that the two masks can preferably move vertically and in concert, thereby allowing rapid, automated adjustment of the different excitation fields. The masks should be mounted so that the diffracting and filtering patterns are aligned at the same height and positioned symmetrically along the optical axis of the system. For example, the two masks may be mounted on a mechanical translation stage whose position can be controlled manually or by using a motorized drive and a computer. In this manner, data can be sequentially taken at a number of wavevectors to allow determination of various points along the dispersion curves of bulk and thin film samples. Alternatively, in order to reduce the number of components of the optical modulating system, both masks can be formed on a single substrate. For example, the diffracting, spatially periodic pattern may be formed on one surface of a glass plate, and the spatially filtering pattern may be formed on the opposing surface. In this case, the diffracting and filtering patterns are positioned relative to each other as described above, and the substrate must be thick enough to allow the diffracted sub-beams to adequately disperse before impinging the spatially filtering surface.

Once data is collected for a particular wavevector, the masks are translated so that new diffracting and filtering patterns are used to generate an excitation field at a new wavevector, and the data-collection process is repeated. Alternatively, a single pattern containing several distinct spatial frequencies may be used to modulate the incident excitation beam, and a second mask is used to select the desired Fourier components of the fields to be imaged onto the sample. In this embodiment, multiple excitation and probe beams, each corresponding to a different excitation wavevector, are diffracted by the first mask, and are then recombined on the sample and used to generate multiple signal beams, which may then be detected and analyzed. This allows the entire dispersion of the sample to be determined during a single excitation probe event.

The optical sources and detection electronics which may be used with the optical modulating system have been described previously in J. A. Rogers et al., J. Appl. Phys. 75:1 (1994) and A.R. Duggal et al., U.S. Ser. No. 07/910, 762, the contents of which are incorporated herein by reference. Briefly, in order to impulsively generate material motions in a sample (using, e.g., ISTS or ISBS), the excitation beam is pulsed, and may be generated using a light source which is Q-switched, mode-locked, or both. The pulse duration of the excitation field must be short enough to impulsively stimulate material motions in the film. For example, in order to excite acoustic processes, the output pulse preferably has a duration of between 100 picoseconds and 5 nanoseconds. The energy of the output pulse is preferably between 0.1 and 5 millijoules. In addition, the repetition rate of the pulses must be high enough to allow suitable data averaging (when necessary), but low enough to allow the thermal properties of the sample to recover between laser shots. Preferably, the repetition rate is between 1 and 2000 Hz, with the rate being adjusted for measurement of different types of samples. For samples which easily damage, such as thin polymer films, it may be preferable to reduce the repetition rate of the excitation laser.

In order to created excited-state transient gratings (e.g., gratings of electron-hole pairs, or other excitonic species), the carrier frequency of the excitation beam is such that it is absorbed by the sample. If the excitation wavelength is below the absorption energy of the sample, the beam may first be passed through one or more non-linear optical devices, such as a frequency-doubling or frequency-tripling crystal, which can be used to generate higher-order harmonics (e.g., second or third order harmonics) of the fundamental frequency. Alternatively, if the sample is excited using mechanisms which do not rely on optical absorption (e.g., ISRS or ISBS processes), the excitation light need not be absorbed by the sample.

Once excited, the time-dependent properties of the sample are recorded by monitoring the time-dependent diffraction of the probe beam, which is preferably derived from a continuous wave (cw) single-mode laser producing between 0.1 and 1 Watt in the visible frequency range (e.g., 514 nm) with a flat intensity profile. In certain embodiments, in order to measure the entire time dependence of the transient grating induced in the sample (which, e.g., may take place over several hundreds of microseconds), a well-defined probe waveform is generated by electro-optically modulating the cw probe beam with a light modulator which controls both the duration and shape of the probe waveform. Preferably, in this case, a probe pulse having a square-wave profile is generated. The waveform has a time duration slightly longer than the time-dependent motions in the film. The pulse preferably has a temporal duration on the order of between 1 and 100 microseconds. Alternatively, a Q-switched laser producing a pulse duration greater than about 100 ns may be used as the probe laser. In this case, the pulse may be frequency doubled or tripled prior to interacting with the sample. In still other embodiments, the diffracted signal may be mapped out in a point-by-point basis, using a pulsed probe beam as described in Duggal et al., U.S. Ser. No. 07/910,762.

The probe waveform diffracted from the transient grating induced in the sample is preferably detected with a time-resolving photodetector. This allows the entire time dependence of the excited region of film to be measured with a single probe waveform. For especially weak signals, a lens may be used to focus the diffracted beam on the optically active region of the detector, thereby increasing the intensity of the signal. For particularly noisy or weak signals, signal-enhancing electronics, such as high-speed amplifiers, may be used in combination with the photodetector. For signals detected on a point-by-point basis, photodetectors having long time constants may be used to generate the light-induced signal.

Light sources other than Nd:YAG lasers may be used to optically excite the film. Suitable lasers include, among others, Nd:YLF, ion (e.g., argon and krypton), Ti:Sapphire, diode, $CO_2$, holmium, excimer, dye, and metal-vapor lasers. Similarly, light sources other than cw argon ion lasers may be used as the probe laser. Alternative lasers include diode and krypton ion lasers. Pulsed light sources which may be used to generate the probe beam include Q-switched Nd:YAG, Nd:YLF, Ti:Sapphire, diode, $CO_2$, holmium, excimer, dye, and metal-vapor lasers.

The samples which may be monitored with the method and apparatus described herein may be bulk (e.g., solids such as metal or semiconductors), thin films (e.g., polyimide, semiconductor, or metal films), fluids, surfaces or other samples exhibiting time-dependent material motions. The material properties which can be determined in these samples include mechanical, elastic, (depth-dependent and/or anisotropic) diffusive, adhesion-based, thermal (e.g., thermal diffusivities) and viscous properties associated with the damping of acoustic waves. In addition, electron relaxation lifetimes, electron-hole recombination times, exciton lifetimes, and bi-exciton lifetimes may additionally be determined in, for example, metal and semiconductor samples.

In bulk systems the dispersion of the acoustic properties allows the frequency dependence of the mechanical (e.g., bulk or shear) modulus to be determined. Additionally, measurement of the thermal diffusion dynamics allows the thermal diffusivity for the bulk system to be determined. In thin film systems, the acoustic information that is obtained allows determination of the degree of adhesion, delamination properties, and the elastic, shear, and longitudinal moduli, as well as anisotropies in these properties. Depth-dependent properties and residual stresses in thin films can also be determined.

The following are examples of the use of the optical modulating system to generate and measure transient motions in bulk and thin film samples.

EXAMPLES

The material motions of thin polyimide film samples adhered to silicon substrates were measured by passing an excitation beam through the optical modulating system described herein, resulting in the excitation of a transient grating in the sample. Following excitation, the temporal dynamics of the grating were monitored using a probe beam delivered to the sample using a separate optical system.

In the data reported, waveguide modes in the film were excited using a Q-switched, mode-locked, and cavity-dumped Nd:YAG laser. The output pulse had an energy of 1 millijoule, a wavelength of 1064 nm, a pulse duration of 100 ps, and a repetition rate of up to 1 kHz. The light from this laser was first attenuated and then passed through a lithium triborate (LBO) crystal to yield light at 532 nm, which was then mixed with the remnant 1064 nm radiation in a β-barium borate (BBO) crystal to yield excitation pulses of approximately 20 microjoules at 355 nm. This light was then attenuated to yield ~1 microjoule pulses that were used for excitation of the films.

The excitation pulses were focussed on the patterned region of the mask using a cylindrical lens having a focal length of 15 cm to produce a beam size of about 1 cm (z direction) by 300 microns (x direction). The patterned region permitted modulation of the amplitude of the excitation beam, and consisted of alternating light-absorbing regions spaced by transparent regions, resulting in a pattern having a square-wave spatial profile. In the patterned region, the light-absorbing regions were spaced by a distance of 6 microns, with each region having a width of 6 microns. The light-absorbing regions of the second patterned region of this same mask were spaced by a distance of 12 microns, with each region having a width of 12 microns. The second mask was spaced by a distance of 2 cm from the first mask, and contained a series of two square openings for spatial filtering of the diffracted excitation sub-beams. In the first series of openings, the transmitting regions had an area of 1 $cm^2$ and were spaced by a distance of 4 cm. The transmitting regions of the second series had an area of 1 cm and were spaced by a distance of 2 cm.

The imaging system used to image the spatial patterns of the masks onto the sample consisted of a single lens having a focal length of 20 cm. The lens was separated from the first mask by a distance of 40 cm. The imaging lens was displaced by a distance of 40 cm from the sample. Recombination of the excitation sub-beams using this imaging system and the two masks resulted in spatially varying optical excitations patterns at the sample having wavevectors equal to the spatial frequency of the patterned regions of the masks.

Material motions in the film were recorded in real-time by monitoring the time-dependent diffraction of a probe pulse spatially overlapped with the induced transient grating. The probe pulse had a duration of about 150 ns, and was derived from Q-switched Nd:YAG laser. Prior to irradiating the sample, the probe beam was frequency-doubled to a wavelength of 532 nm. The probe beam was then focussed at an angle of 15° to a 100-micron diameter spot on the transient grating. The diffracted component of the probe beam was measured with a fast amplified photodiode (Antel; 2 GHz bandwidth). The light-induced signal was then sent to a transient digitizer (Tektronics DSA 602A; 1 GHz bandwidth), resulting in generation of digital signal for analysis. The combination of the photodiode and transient digitizer effectively provided a 1 GHz-bandwidth window through which the film's oscillatory and relaxational motions were monitored.

Figure 6A:
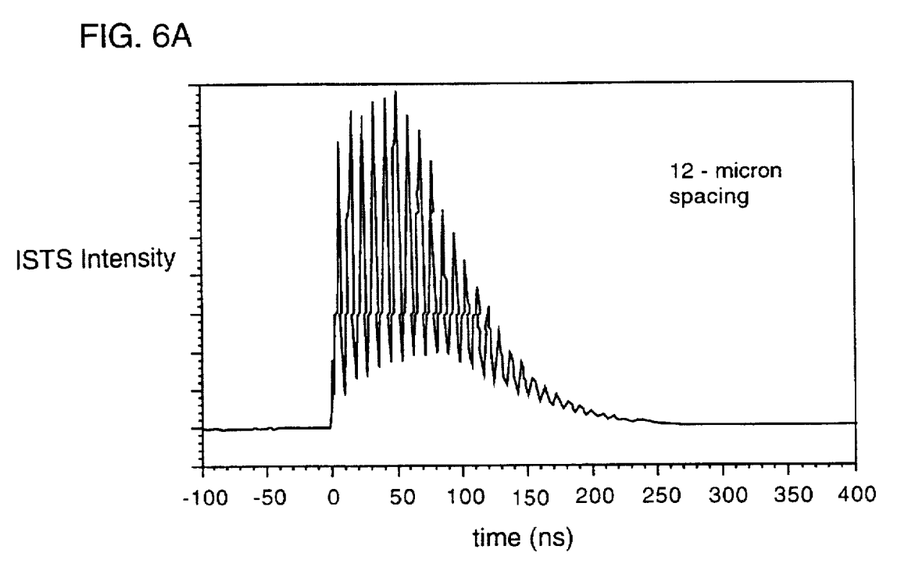
FIGS. 6A and 6B are, respectively, plots showing the time dependence of the diffracted signal from a thin grating generated in a film sample using the optical modulating system.
Figure 6B:
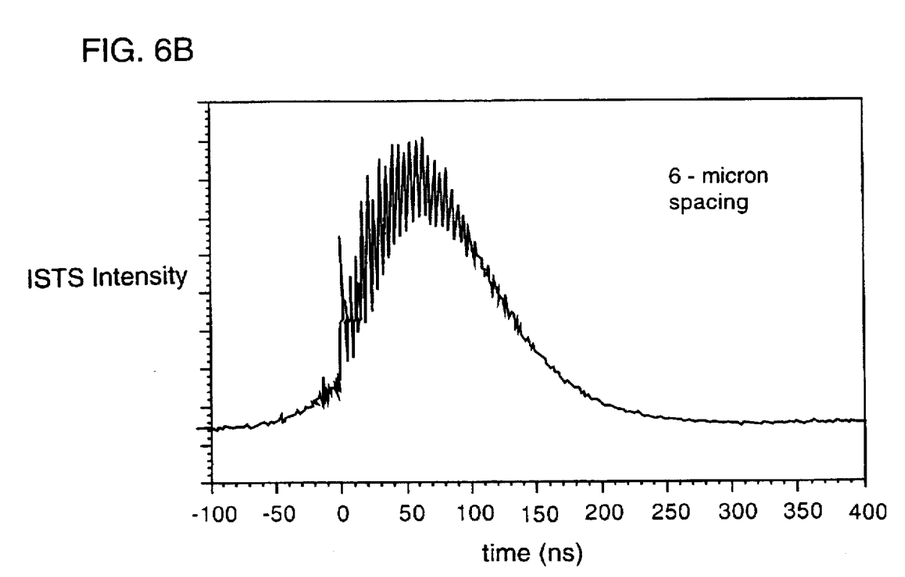

Data was generated by passing the excitation beam through the first set of patterns on the two masks, signal averaging for 20 laster shots, and then mechanically adjusting the masks so that the excitation beam was modulated by the second set of patterns. Referring now to FIGS. 6A and 6B, typical data taken from the silicon-bound polyimide films using the above-identified optical system illustrates the time-dependent nature of the measured signal. The oscillatory component of the data is due to the coherent, periodic motions of the excited waveguide modes. The difference in frequency between the two data scans is due to excitation of the film with different wavevectors. Damping of these modes, shown in the data (after several hundred nanoseconds) as a decrease in the amplitude of subsequent oscillations, is due to viscous losses in the polyimide material. The two data scans, taken with different excitation wavevectors adjusted during a time period of just 19 seconds, demonstrate that the optical modulation system can be used to change the wavevector of the excitation pattern in very rapid fashion, and can additionally be used to generate data having high signal-to-noise ratios.

In a separate experiment, the first and second masks described above were used to sequentially modulate the excitation and probe beams in order to monitor the response of the liquid salol at room temperature. In this case, the sample was optically excited throughout the bulk (i.e., in the thick-grating regime) using the fundamental frequency from the Nd:YAG laser described above. The transient grating was probed using the output from a cw single-mode Argon ion laser (Lexel 3500) producing 1 Watt at 514 nm with a flat intensity profile. This output was electro-optically modulated (Conoptics 380) to yield a square pulse having a temporal width of 100 microseconds. The signal beam was detected using the photodetector and transient digitizer described above. In this experiment, the excitation and probe beams were made collinear prior to modulation with the diffracting and spatial filtering masks, and 1:1 imaging optics (i.e. M=1) were used, thereby ensuring that the phase-matching criteria were satisfied by the probe beam.

Figure 7A:
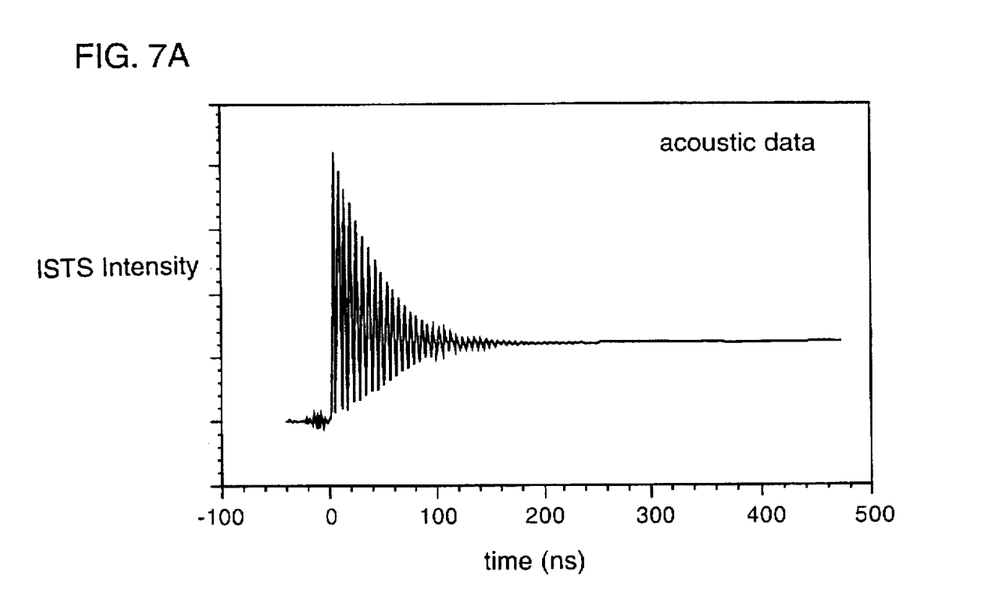
FIGS. 7A and 7B are, respectively, plots showing the time dependence of the diffracted signal from a thick grating generated in salol using the optical modulating system.
Figure 7B:
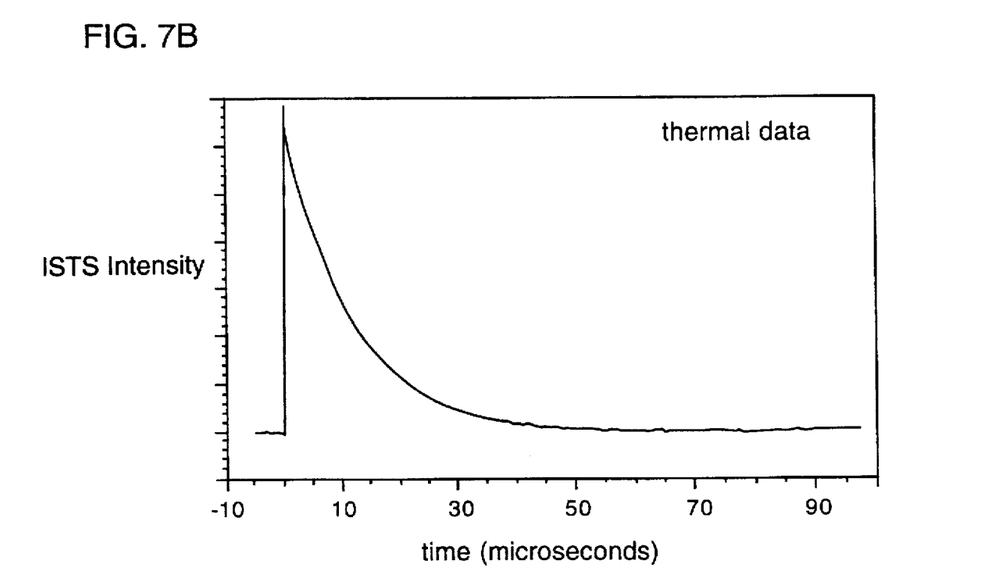

Referring now to FIGS. 7A and 7B, two sets of data were generated using a first mask with amplitude-modulating regions 6 microns wide, and 6 microns apart. The second mask used to filter the diffracted beam had two openings, each with an area of 1 cm$^2$ and spaced by a distance of 4 cm. The first order diffracted components of the pattern on the first mask were imaged onto the sample, resulting in a sinusoidally varying excitation field having a spatial periodicity of 6 microns. The diffracted signals were measured during short (i.e., 600 ns; FIG. 7A) and long (i.e., 110 microseconds; FIG. 7B) time windows.

The high signal-to-noise ratios of the data scans illustrates that the Bragg angle is accurately set using the masks. (If the probe were not incident at the Bragg angle, the diffracted signal would be too weak to measure.) In the experiments, the residual probe sub-beam overlapped with the signal beam was used as a finder beam to allow facile alignment of the signal into the photodetector. As before, the coherent oscillations in the data were due to the induced acoustic processes in the samples, while the long-time exponential decay is due to thermal diffusion.

Other embodiments are within the scope of the following claims.

What is claimed is:

1. A method of determining a property of a sample, said method comprising:
   (a) providing an excitation beam of radiation and then passing the beam through a pattern on a diffracting mask to form at least two excitation sub-beams;
   (b) overlapping at least two excitation sub-beams on a region of the sample with an imaging system to generate a spatially varying optical field which is an image of the pattern and which excites a transient grating in the region of the sample;
   (c) irradiating the transient grating with a probe beam of radiation oriented so that at least a portion of the probe beam is diffracted by the transient grating;
   (d) detecting the diffracted portion of the probe beam with an optical detector to generate a light-induced signal; and
   (e) analyzing said light-induced signal from the optical detector to determine the property of the sample.

2. The method of claim 1, wherein the pattern on the diffracting mask comprises alternating light-modulating regions characterized by at least one spatial frequency, and the excitation beam is separated into at least a zeroth, +1, and −1 excitation sub-beam by diffracting the excitation beam off of the light-modulating regions of the diffracting pattern.

3. The method of claim 2, wherein said overlapping step further comprises the step of passing at least the +1 and −1 excitation sub-beams through the imaging system prior to overlapping the excitation sub-beams on the sample.

4. The method of claim 3, wherein the imaging system images at least one of the spatial frequencies of the light-modulating regions of the diffracting pattern onto the sample to form the spatially varying optical field.

5. The method of claim 4, wherein at least one of the spatial frequencies of the light-modulating region and the spatial varying optical field are equivalent.

6. The method of claim 3, wherein the imaging system comprises a lens which focuses the excitation sub-beams on the sample.

7. The method of claim 1, wherein the excitation beam is focussed onto the pattern on the diffracting mask prior to step (a).

8. The method of claim 7, wherein the excitation beam is cylindrically focussed onto the pattern on the diffracting mask.

9. The method of claim 2, wherein the probe and excitation beams are made collinear prior to step (a).

10. The method of claim 9, wherein step (a) further comprises the step of separating the probe beam into at least two probe sub-beams by passing the probe beam through the pattern on the diffracting mask.

11. The method of claim 9, wherein said probe sub-beams pass through the imaging system prior to irradiating the grating induced in the region of the sample.

12. The method of claim 11, wherein the imaging system is a 1:1 imaging system.

13. The method of claim 12, wherein the probe beam irradiates the transient grating at the Bragg angle.

14. The method of claim 10, wherein between steps (a) and (b) said excitation sub-beams are spatially filtered with a second mask.

15. The method of claim 14, wherein the diffracting mask and second mask are part of a single unit.

16. The method of claim 14, wherein the pattern on the diffracting mask comprises alternating light-modulating regions characterized by at least one spatial frequency, and the excitation beam is separated into at least a zeroth, +1, and −1 excitation sub-beam by diffracting the excitation beam off of the light-modulating regions of the diffracting pattern, and wherein said spatial filtering transmits the +1 and −1 excitation sub-beams and probe sub-beam.

17. The method of claim 1, wherein the excitation and probe beams have the same wavelength.

18. The method of claim 1, wherein the excitation and probe beams have different wavelengths.

19. The method of claim 18, wherein the wavelengths of the excitation and probe beams are partially absorbed by the sample.

20. The method of claim 1, wherein said analyzing step further comprises determining a dispersion of the sample.

21. The method of claim 20, wherein the dispersion is used to determine the mechanical, thermal, optical, or electronic properties of the sample.

22. The method of claim 21, wherein the mechanical property is one of adhesion, elastic moduli, stiffness, residual stress, and density.

23. The method of claim 20, wherein the dispersion is determined following inducing multiple transient gratings in the sample with a single spatial varying optical field having multiple spatial frequencies.

24. The method of claim 20, wherein the dispersion is determined following sequentially inducing multiple transient gratings in the sample with multiple spatial varying optical fields, each having a single spatial frequency.

25. A method of diffracting a probe beam off a sample, said method comprising:
   (a) providing a beam of radiation and then passing the beam through a pattern on a diffracting mask to form at least two excitation sub-beams;
   (b) overlapping at least two excitation sub-beams on a region of the sample with an imaging system to generate a spatially varying optical field which is an image of the diffracting pattern and which is an image of the diffracting pattern and which excites a transient grating in the region of the sample; and
   (c) irradiating the transient grating with a probe beam oriented so that at least a portion of the probe beam is diffracted by the transient grating.

26. An apparatus for diffracting a portion of a probe beam off a sample, comprising:

means for generating a probe optical beam and an excitation optical beam orientated along an optical axis;

a diffracting mask comprising an optical diffracting pattern, said diffracting pattern being positioned along the optical axis and being configured so that when irradiated with the excitation beam, said pattern diffracts the excitation beam to generate at least two excitation sub-beams;

an imaging system comprising at least one lens positioned along the optical axis, said imaging system configured to focus the excitation sub-beams onto a region of the sample to generate a spatially varying optical field which is an image of the diffracting pattern and which excites a transient grating in the region of the sample, said grating allowing diffraction of a portion of the probe beam off of the excited region of the sample.

27. The apparatus of claim 26, wherein said diffracting pattern comprises a series of opaque regions spaced by a distance which allows diffraction of visible or infrared radiation.

28. The apparatus of claim 26, wherein said diffracting pattern comprises a series of regions etched to a depth and spaced by a distance which allows diffraction of visible or infrared radiation.

29. The apparatus of claim 26, wherein said diffracting mask comprises a plurality of diffracting patterns.

30. The apparatus of claim 26, wherein said apparatus further comprise a spatially filtering mask comprising a pair of openings, said opening positioned along the optical axis so that said spatially filtering mask allows spatial filtering of said diffracted excitation sub-beams.

31. The apparatus of claim 30, wherein the diffracting and spatial filtering masks are comprised in a single unit.

32. The apparatus of claim 30, wherein said filtering mask comprises a plurality of pairs of openings.

* * * * *